United States Patent [19]

Routh et al.

[11] Patent Number: 5,772,691
[45] Date of Patent: Jun. 30, 1998

[54] IMPLANTABLE CARDIAC STIMULATOR WITH POLARITY DETECTION FOR DETECTING ECTOPIC BEATS

[75] Inventors: Andre Routh, Lake Jackson, Tex.; Annette Bruls, Brussels, Belgium; Drury Woodson, III, Alvin; Joseph Vandegriff, Brazoria, both of Tex.; Yves Verboven, Kessel-lo, Belgium; Parick J. Paul, Lake Jackson, Tex.

[73] Assignee: Sulzer Intermedics inc., Angleton, Tex.

[21] Appl. No.: 843,235

[22] Filed: Apr. 14, 1997

[51] Int. Cl.⁶ .................................................. A61N 1/362
[52] U.S. Cl. ............................................................ 607/9
[58] Field of Search .................... 607/9, 14; 600/515, 600/509, 517

[56] References Cited

U.S. PATENT DOCUMENTS

| | | | |
|---|---|---|---|
| 4,510,945 | 4/1985 | Barreras | 600/509 |
| 4,527,568 | 7/1985 | Rickards | 128/419 |
| 4,663,701 | 5/1987 | Stotts | 363/60 |
| 4,856,523 | 8/1989 | Sholder et al. | 128/419 |
| 4,903,699 | 2/1990 | Baker, Jr. et al. | 128/419 |
| 4,913,145 | 4/1990 | Stotts | 128/419 |
| 5,010,887 | 4/1991 | Thornander | 600/509 |
| 5,052,388 | 10/1991 | Sivula et al. | 128/419 |
| 5,103,819 | 4/1992 | Baker et al. | 128/419 |
| 5,190,052 | 3/1993 | Schroeppel | 128/786 |
| 5,350,409 | 9/1994 | Stoop et al. | 607/17 |
| 5,391,189 | 2/1995 | van Krieken et al. | 607/17 |
| 5,395,393 | 3/1995 | Wickham | 607/9 |
| 5,400,796 | 3/1995 | Wecke | 600/509 |
| 5,431,693 | 7/1995 | Schroeppel | 607/28 |
| 5,443,485 | 8/1995 | Housworth et al. | 607/28 |
| 5,513,644 | 5/1996 | McClure et al. | 600/521 |
| 5,543,795 | 8/1996 | Fernald | 341/163 |
| 5,560,369 | 10/1996 | McClure et al. | 600/517 |
| 5,571,144 | 11/1996 | Schroeppel | 607/28 |

OTHER PUBLICATIONS

Larry J. Stotts; Introduction to Implantable Biomedical IC Design; Jan., 1989; pp. 12–19; IEEE Circuits and Devices Magazine.

Primary Examiner—William E. Kamm
Assistant Examiner—Kennedy J. Schaetzle
Attorney, Agent, or Firm—John R. Merkling

[57] ABSTRACT

An implantable medical device for electrically stimulating the heart to beat including a sense circuit for detecting cardiac electrical activity. The sense circuit includes a sense amplifier, band pass filter, and threshold detector. The threshold detector determines whether sensed cardiac electrical activity resulted from a normal heart beat or an ectopic beat such as a premature ventricular contraction. In a preferred embodiment, latches in the threshold detector are activated by output pulses from a pair of comparators. A positive comparator produces an output pulse upon detection of cardiac electrical activity exceeding a positive threshold voltage and a negative comparator produces an output pulse upon detection of cardiac electrical activity more negative than a negative threshold. Threshold logic produces output signals indicative of which comparator first produced an output pulse. A logic and control unit monitors the output signals from the threshold logic and thus determines whether the associated cardiac electrical activity represented a normal heart beat or resulted from an ectopic beat so that appropriate pacing may be provided by the implantable device.

9 Claims, 6 Drawing Sheets

IMPLANTABLE CARDIAC STIMULATOR WITH POLARITY DETECTION FOR DETECTING ECTOPIC BEATS

BACKGROUND OF THE INVENTION

1. Field of the Invention

The present invention relates generally to cardiac stimulating devices, such as pacemakers and defibrillators. More particularly, the present invention relates to a cardiac stimulating device that detects electrical activity in the heart. Still more particularly, the present invention relates to a cardiac stimulating device that can distinguish normal heart beats from abnormal ectopic beats.

2. Description of the Related Art

Figure 1:
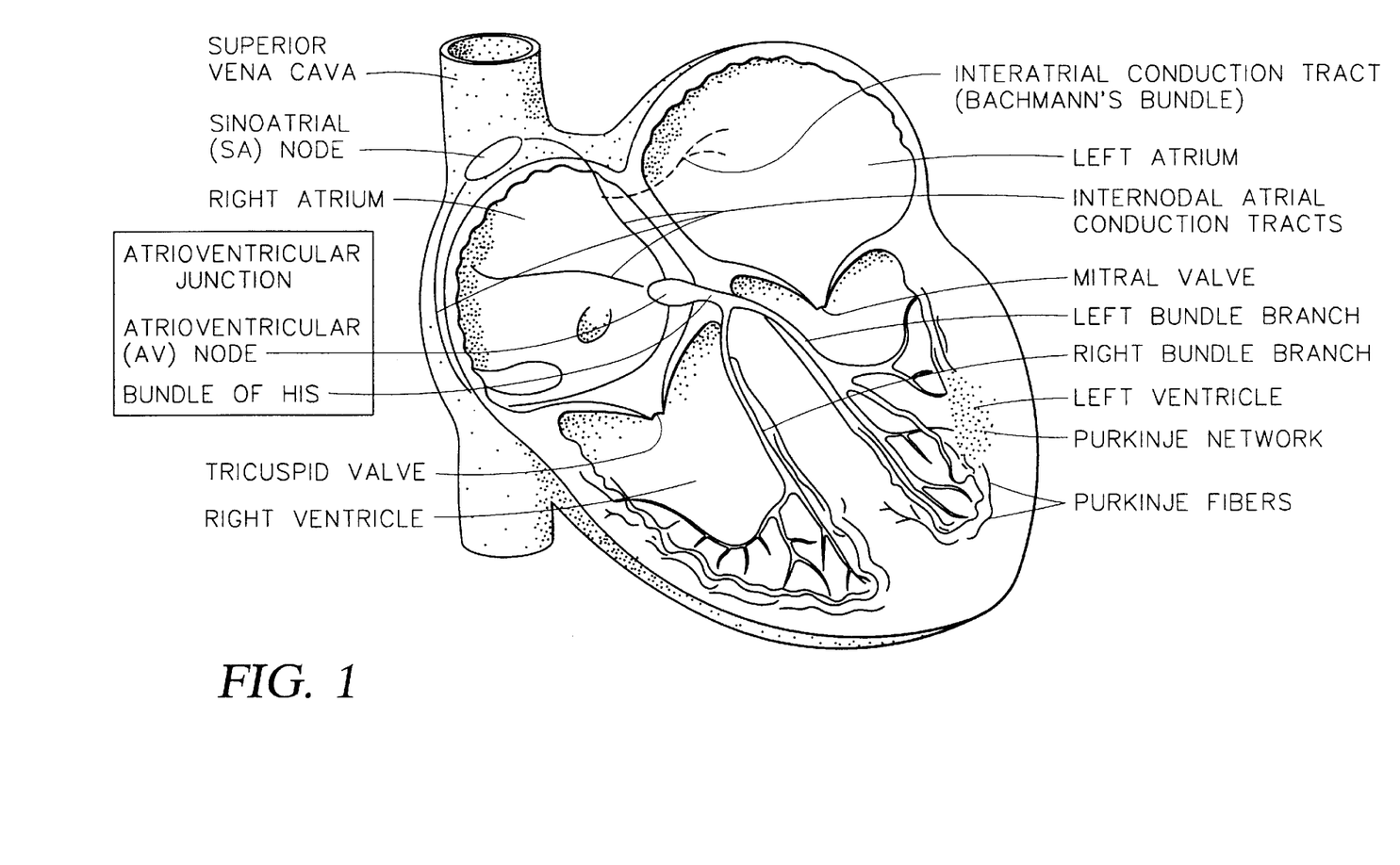
FIG. 1 is a schematic cut-away view of a human heart, in which the various relevant parts are labeled.

In the normal human heart, illustrated in FIG. 1, the sinus (or sinoatrial (SA)) node generally located near the junction of the superior vena cava and the right atrium constitutes the primary natural pacemaker by which rhythmic electrical excitation is developed. The cardiac impulse arising from the sinus node is transmitted to the two atrial chambers (or atria) at the right and left sides of the heart. In response to excitation from the SA node, the atria contract, pumping blood from those chambers into the respective ventricular chambers (or ventricles). The impulse is transmitted to the ventricles through the atrioventricular (AV) node, and via a conduction system comprising the bundle of His, or common bundle, the right and left bundle branches, and the Purkinje fibers. The transmitted impulse causes the ventricles to contract, the right ventricle pumping unoxygenated blood through the pulmonary artery to the lungs, and the left ventricle pumping oxygenated (arterial) blood through the aorta and the lesser arteries to the body. The right atrium receives the unoxygenated (venous) blood. The blood oxygenated by the lungs is carried via the pulmonary veins to the left atrium.

This action is repeated in a rhythmic cardiac cycle in which the atrial and ventricular chambers alternately contract and pump, then relax and fill. Four one-way valves, between the atrial and ventricular chambers in the right and left sides of the heart (the tricuspid valve and the mitral valve, respectively), and at the exits of the right and left ventricles (the pulmonic and aortic valves, respectively, not shown) prevent backflow of the blood as it moves through the heart and the circulatory system.

The sinus node is spontaneously rhythmic, and the cardiac rhythm it generates is termed normal sinus rhythm ("NSR") or simply sinus rhythm. This capacity to produce spontaneous cardiac impulses is called rhythmicity, or automaticity. Some other cardiac tissues possess rhythmicity and hence constitute secondary natural pacemakers, but the sinus node is the primary natural pacemaker because it spontaneously generates electrical pulses at a faster rate. The secondary pacemakers tend to be inhibited by the more rapid rate at which impulses are generated by the sinus node.

Disruption of the natural pacemaking and propagation system as a result of aging or disease is commonly treated by artificial cardiac pacing, by which rhythmic electrical discharges are applied to the heart at a desired rate from an artificial pacemaker. An artificial pacemaker (or "pacer" as it is commonly labeled) is a medical device which delivers electrical pulses to an electrode that is implanted adjacent to or in the patient's heart in order to stimulate the heart so that it will contract and beat at a desired rate. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart. An in-depth explanation of certain cardiac physiology and pacemaker theory of operation is provided in U.S. Pat. No. 4,830,006.

Pacers today are typically designed to operate using one of three different response methodologies, namely, asynchronous (fixed rate), inhibited (stimulus generated in the absence of a specified cardiac activity), or triggered (stimulus delivered in response to a specified hemodynamic parameter). Broadly speaking, the inhibited and triggered pacemakers may be grouped as "demand" type pacemakers, in which a pacing pulse is only generated when demanded by the heart. To determine when pacing is required by the pacemaker, demand pacemakers may sense various conditions such as heart rate, physical exertion, temperature, and the like. Moreover, pacemakers range from the simple fixed rate, single chamber device that provides pacing with no sensing function, to highly complex models that provide fully automatic dual chamber pacing and sensing functions. The latter type of pacemaker is the latest in a progression toward physiologic pacing, that is, the mode of artificial pacing that most closely simulates natural pacing.

Because of the large number of options available for pacer operation, an industry convention has been established whereby specific pacer configurations are identified according to a code comprising three, four or five letters. The fifth code position describes the antitachycardia functions, if any. Because this position is not applicable to most commonly used pacemaker types, most common codes comprise either three or four letters. For this reason and for simplicity's sake, the fifth code position is omitted from the following table. Each code can be interpreted as follows:

| Code position | 1 | 2 | 3 | 4 |
|---|---|---|---|---|
| Function identified | chamber paced | chamber sensed | response to sensing | programmability, rate modulation |
| Options available | 0-none | 0-none | 0-none | 0-none |
| | A-atrium | A-atrium | T-triggered | P-programmable |
| | V-ventricle | V-ventricle | I-inhibited | M-multiprogrammable |
| | D-dual | D-dual | D-dual | C-communicating |
| | (A + V) | (A + V) | (T + I) | R-rate modulating |

For example, typical treatment for patients experiencing either atrial bradyarrythmias with or without A–V block, or normal sinus rhythm with A–V block, generally includes using a DDD pacer. A DDD pacer paces either chamber (atrium or ventricle) and senses in either chamber. Thus, a pacer in DDD mode, may pace the ventricle in response to electrical activity sensed in the atrium. By pacing the ventricle in response to atrial activity (presumably resulting from or occurring during atrial contraction), proper synchronization is maintained between the atria and ventricles, and blood is efficiently pumped through the circulatory system. For DDD mode pacers to function properly, accurate detection of atrial contractions is required.

Figure 2:
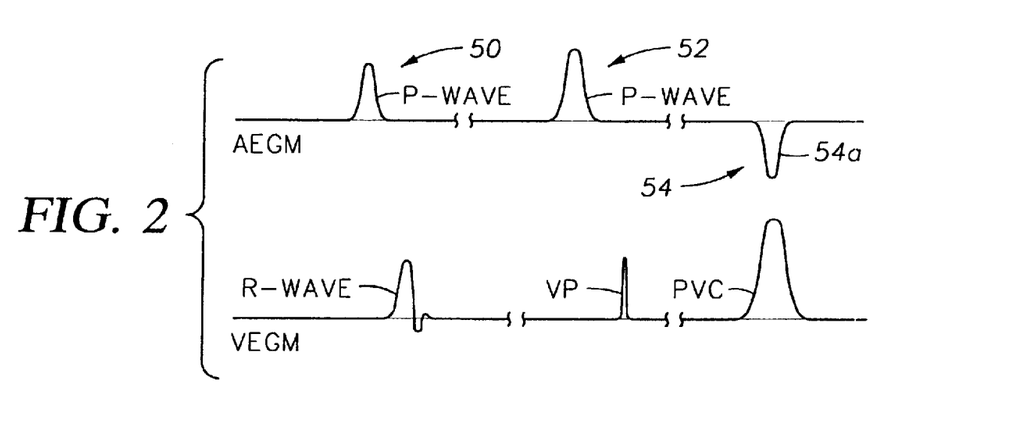
FIG. 2 shows exemplary atrial and ventricular electrograms including normal atrioventricular coordination, DDD pacing, and a premature ventricular contraction.

Exemplary rhythms of the electrical activity in the atrium and ventricle are shown in FIG. 2. A rhythm representing atrial electrical activity is termed an "atrial electrogram" or "AEGM". An AEGM typically is measured by implanting a pair of electrodes in the left atrium and amplifying the signal received by the pair of electrodes. Similarly, a ventricular electrogram is termed VEGM and is measured by a pair of electrodes implanted in the ventricles. During event 50, an electrical pulse that is generated by the SA node to initiate atrial contraction, commonly called a P-wave, is detected by the atrial electrodes. Following contraction of the atrium, a naturally occurring electrical pulse propagates through the ventricles causing the ventricles to contract. This pulse is referred to as an R wave, is detected by the ventricular electrodes.

DDD pacer operation is exemplified in FIG. 2 by event 52 in which a P-wave is detected by the atrial electrodes and is followed by a ventricular pace (VP) pulse produced by the pacer. Ventricular pace pulse VP causes the ventricles to contract and pump blood into the pulmonary artery and aorta (not specifically shown in FIG. 1). For ventricular contraction to efficiently pump blood, the ventricles first must fill with blood from the atria before the ventricles are forced to contract. The P-wave detected by the atrial electrodes indicates atrial contraction and thus can be used to gauge when the ventricles will be full and ready to be paced. Thus, the pacer paces the ventricles with a VP pulse at an appropriate time interval after the P-wave, typically 150–200 milliseconds.

Effective pacing breaks down if atrial activity detected by the atrial electrodes is registered by the pacer as a P-wave from the SA node when, in fact, the origin of the electrical activity was from a site other than the SA node. Such sites of abnormally-originating electrical activity are commonly called "ectopic" sites, and the resulting electrogram rhythm is called an "ectopic beat." There are numerous causes of ectopic beats such as premature atrial beats and premature ventricular contractions (PVC). An exemplary PVC is shown in the VEGM of FIG. 2 in event 54. PVCs normally originate in some part of the specialized ventricular propagating system or in damaged tissue around myocardial infarcts. The electrical pulse causing the PVC propagates through the ventricle exciting the ventricles to contract. The pulse may further move into the atria and be detected by the atrial electrodes as pulse 54*a*. The polarity of a pulse detected by the atrial electrodes from an ectopic source depends on the location of the ectopic site relative to the atrial electrodes, as described below.

Figure 3:
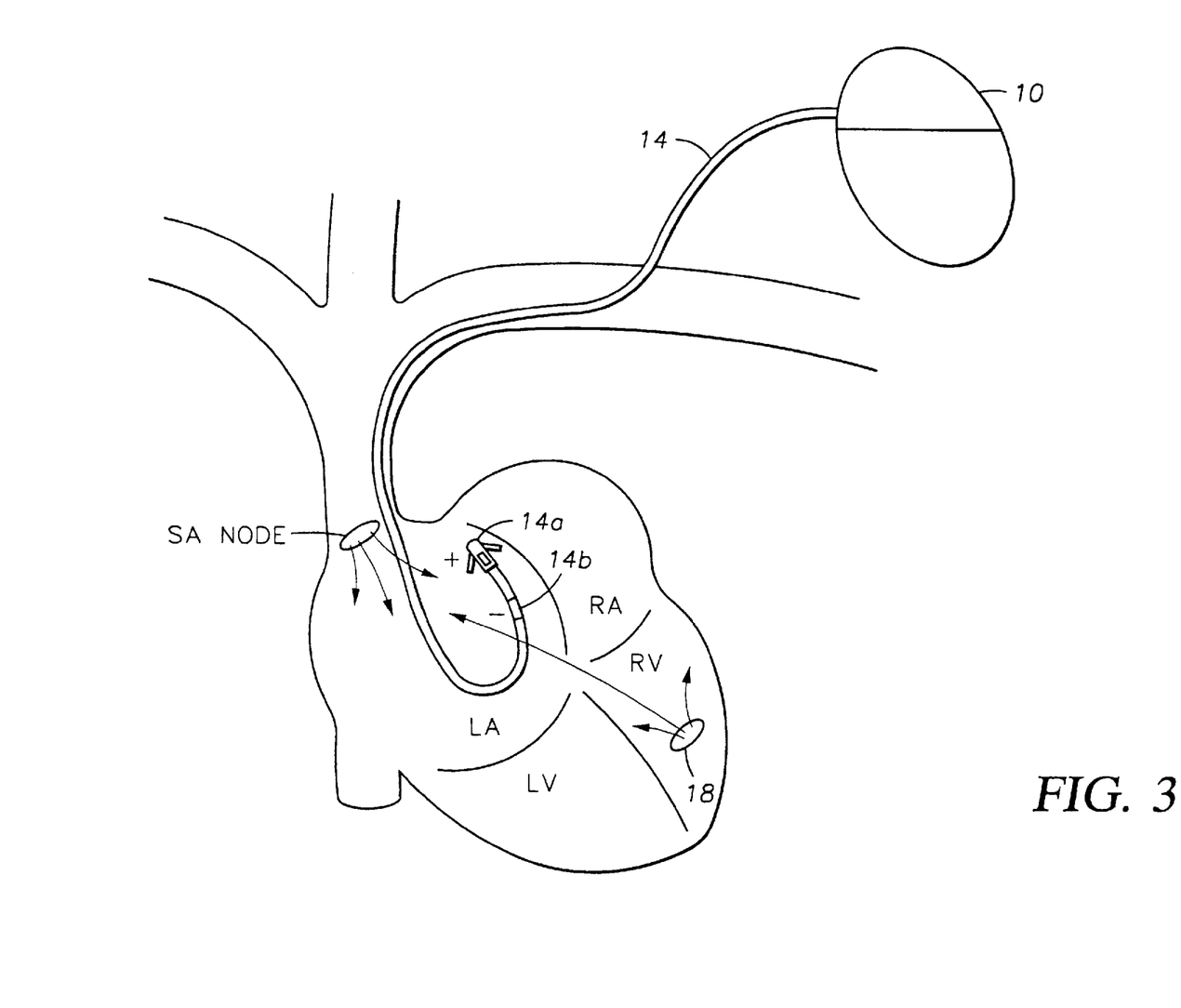
FIG. 3 is a schematic diagram of the heart showing atrial electrodes in relation to the SA node and the site of a premature ventricular contraction.

Referring now to FIG. 3, a schematic view of a heart is shown to include the four chambers of the heart: left atrium (LA), left ventricle (LV), right atrium (RA), and right ventricle (RV). Pacer 10 is shown with only a single atrial lead 14 for simplicity. When a pulse is generated by the SA node, the pulse's wave front propagates in the direction of the arrows, generally in the direction from the tip electrode 14*a* to the ring electrode 14*b*. If the tip electrode 14*a* is given a positive polarity with respect to the ring electrode 14*b*, a positive pulse is detected by the electrodes as the wave front from the SA node passes by the electrodes. Conversely, if a pulse is produced from an ectopic site such as exemplary site 18 and propagates toward the left atrium as indicated, the wave front will impinge on the ring electrode 14*b* first and then move to the tip electrode 14*a* resulting in a pulse detected by electrodes 14*a*, 14*b* of negative polarity. PVCs originate in the ventricles and, given the electrode orientation shown in FIG. 4, thus usually cause the detection of a negative pulse by the atrial electrodes as shown by negative pulse 54*a* in FIG. 2.

Pacemakers usually include threshold detectors that produce a single detect signal when the magnitude of the electrogram exceeds either positive or negative threshold levels. That is, a detect signal is produced when either the electrogram voltage is more positive than a positive threshold level or more negative than a negative threshold level. Typically, the detect signal does not encode whether the detected event was a naturally occurring positive P-wave or a negative pulse resulting from an ectopic site, such as caused by a PVC. Thus, prior pacers were susceptible to incorrectly characterizing negative pulse 54*a* as a naturally occurring P-wave. In a DDD pacer, this mischaracterization results in the ventricles being unnecessarily and undesirably paced.

In sum, electrical activity originating from ectopic sites, as well as electrical activity originating from the SA node, may be detected by the atrial electrodes. The activity from ectopic sites is potentially confused from normally occurring SA node initiated activity, and may cause the pacer to function inappropriately. It would thus be advantageous for a pacer to discern ectopic pulses from SA node initiated pulses, such that ectopic beats could be ignored or dealt with appropriately.

SUMMARY OF THE INVENTION

Accordingly, there is herein provided an implantable medical device such as a pacemaker for electrically stimulating the heart to beat. The implantable medical device includes an atrial sense circuit for detecting and monitoring electrical activity in the atria of the heart, commonly known as the atrial electrogram. The atrial sense circuit includes a sense amplifier, band pass filter, and a threshold detector and provides detect signals to a logic and control unit upon detecting electrical activity in the atria. Additionally, the threshold detector includes threshold logic to distinguish electrical activity originating at the heart's natural pacemaker (SA node) from electrical activity originating at ectopic sites, such as PVCs.

In a preferred embodiment, a plurality of latches in the threshold detector are activated by output pulses from a pair of comparators. A positive comparator produces an output pulse upon detection of cardiac electrical activity exceeding a positive threshold voltage, and a negative comparator produces an output pulse upon detection of cardiac electrical activity more negative than a negative threshold. The threshold logic produces output signals indicative of which comparator first produced an output pulse. The logic and control unit monitors the output signals from the threshold logic and thus determines whether the associated cardiac electrical activity represented a normal heart beat or resulted from an ectopic beat so that pacing may be appropriately controlled.

BRIEF DESCRIPTION OF THE DRAWINGS

Other objects and advantages of the invention will become apparent upon reading the following detailed description and upon reference to the accompany drawings, wherein:

FIG. 6(*a*) shows an exemplary electrogram, including a positive P-wave and a negative pulse resulting from an ectopic source;

FIG. 6(b) shows the output signal produced by the band pass filter of the atrial sense circuit of FIG. 5;

FIGS. 6(c) and 6(d) show output pulses produced by the threshold comparators of the atrial sense circuit of FIG. 5 in response to the band pass filter's output signal of FIG. 6(b)

DETAILED DESCRIPTION OF THE INVENTION

Figure 4:
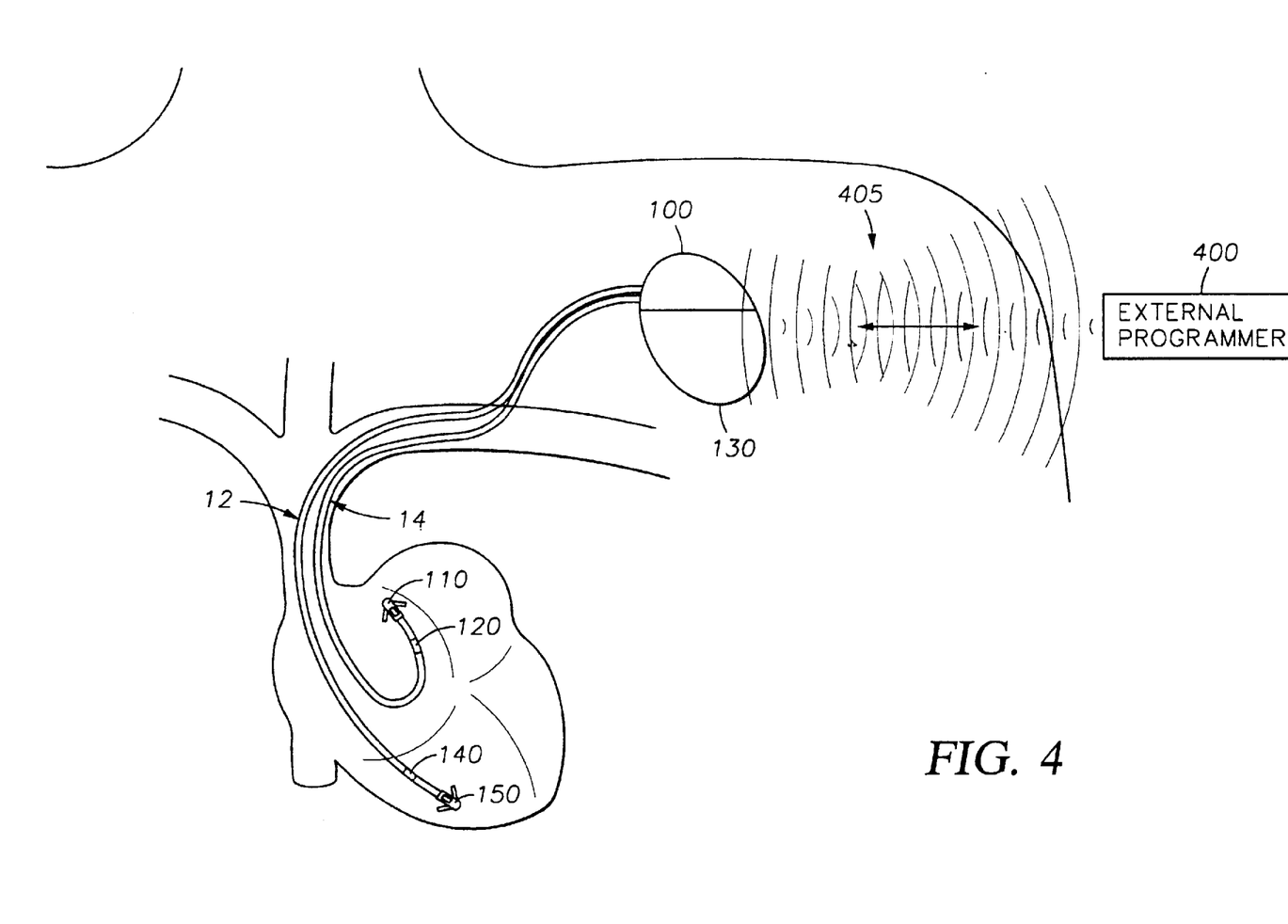
FIG. 4 is a schematic diagram of a pacer constructed in accordance with the invention implanted in a human body and coupled to the heart with electrodes.

Referring now to FIG. 4, an implantable medical device 100 constructed in accordance with the preferred embodiment is shown implanted and coupled to the patient's heart by leads 12, 14. The implantable medical device 100 may include a pacemaker or any medical device that performs pacing functions. For purposes of describing the preferred embodiments of the invention, it will hereafter be described as an implantable pacemaker or simply pacer. However, it should be understood that the invention may likewise be employed in any of a variety of implantable medical devices, such as defibrillators.

In the dual chamber pacing arrangement shown, leads 12, 14 are positioned in the right ventricle and right atrium, respectively. Each lead 12, 14 includes at least one stimulating electrode for delivery of electrical impulses to excitable myocardial tissue in the appropriate chamber(s) in the right side of the patient's heart. As shown in FIG. 4, each lead 12, 14 includes two electrodes. More specifically, lead 14 includes tip electrode 110 and ring electrode 120, and lead 12 includes tip electrode 150 and ring electrode 140. As one skilled in the art will understand, two, three, and four terminal devices all have been used or suggested as possible electrode schemes and may be employed in the present invention.

Figure 5:
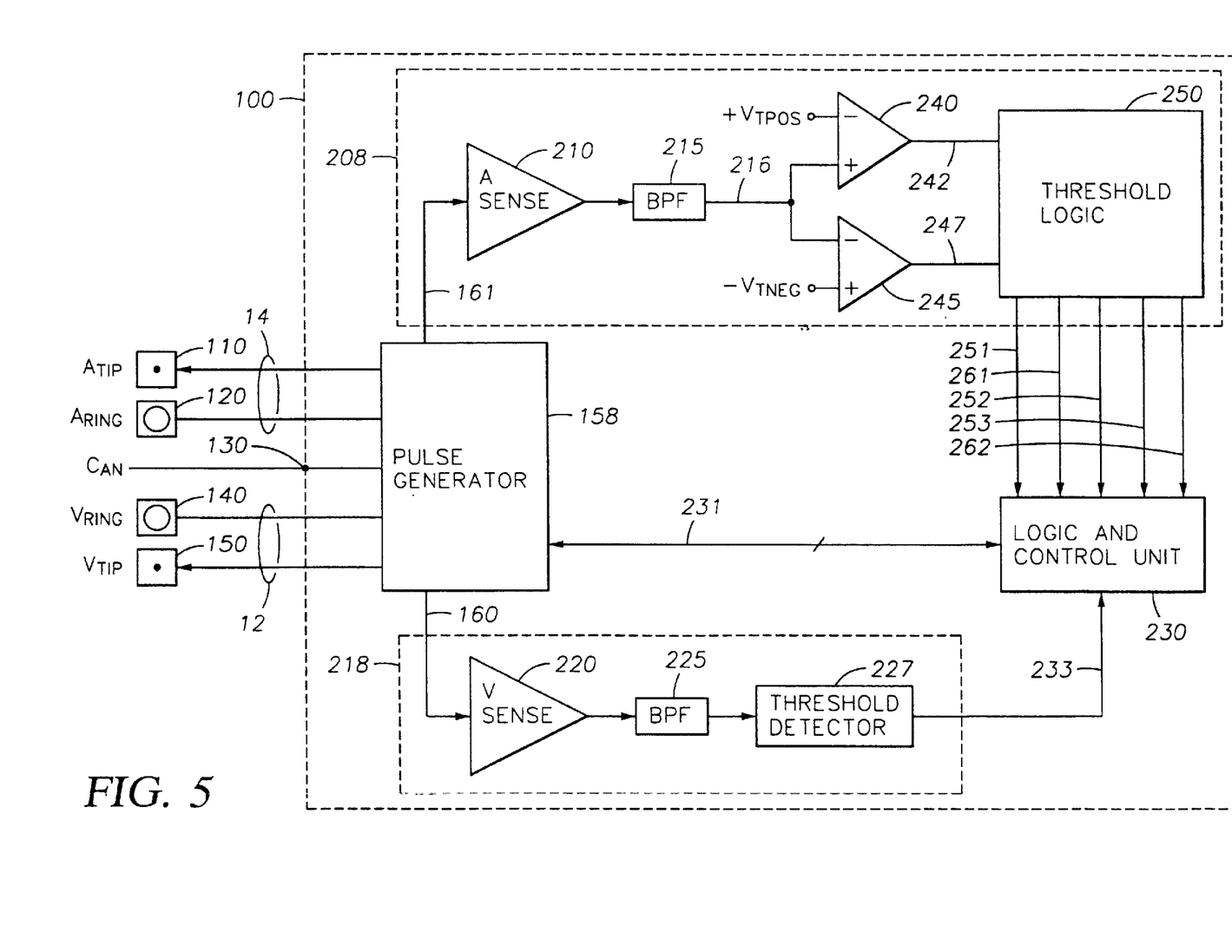
FIG. 5 is a block diagram of the pacer of FIG. 4 having an atrial sense circuit with a band pass filter, threshold comparators, and threshold logic for distinguishing atrial detected events resulting from ectopic beats from atrial events resulting from normal beats.

Referring now to FIG. 5, pacer 100 includes housing or can 130 that houses a conventional battery (not shown), pulse generator 158, atrial sense circuit 208, ventricular sense circuit 218, and logic and control unit 230. Pulse generator 158 delivers the appropriate atrial or ventricular pacing pulses as initiated by logic and control unit 230 to the heart generally through one or more electrodes 110, 120, 140, 150 or can 130 which itself may be employed as an electrode in a conventional manner. Pulse generators are well known in the art and typically include voltage multipliers, voltage regulators, rate limiters, and output switches. Pulse generator 158 preferably is capable of unipolar or bipolar pacing of either the atrium or ventricle. Pulse generator 158 is controlled by logic and control unit 230 via control lines 231. Logic and control unit 230 initiates pacing. Pulse generator 158 delivers a pacing pulse of certain amplitude and time duration (i.e., pulse width). Logic and control unit 230 determines the amplitude and pulse width of the pacing pulse and provides that information to pulse generator 158 over control lines 231.

Atrial sense circuit 208 provides an indication on line 251 to logic and control unit 230 when the atrium contracts. Similarly, ventricular sense circuit 218 indicates to logic and control unit 230 on line 233 when the ventricles contract. Signals on lines 252, 253 indicate whether a P-wave or an ectopic beat have been detected, as explained in detail below.

Referring still to FIG. 5, pacer 100 preferably is a demand-type pacemaker and paces the heart in response to one or more physiological signals or parameters such as heart rate and activity level. Activity level may be determined from an activity sensor (not shown), from thoracic impedance measurements, or other commonly known techniques. Sense circuits 208, 218 amplify and filter signals from the electrodes 110, 120, 140, 150 and provide signals to logic and control unit 230 indicative of electrical activity in the heart. Ventricular sense circuit 218 includes a ventricular sense amplifier 220, band pass filter 225, and threshold detector 227. Ventricular sense circuit 218 receives a signal from pulse generator 158 on line 160 representing the electrical activity in the ventricle in the vicinity of the ventricular electrodes 140, 150. Ventricular sense amplifier 220 preferably is a low power amplifier operating from a power supply of approximately one microampere of current. A suitable sense amplifier is disclosed in U.S. Pat. No. 4,913,145, incorporated herein by reference.

Band pass filter 225 of ventricular sense circuit 218 preferably is a switched capacitor filter such as that disclosed in U.S. Pat. No. 4,913,145, or any other suitable low power, reliable filter suitable for use in implantable pacemakers. The transition in the frequency response of band pass filter 225 between the pass band (in which signals of frequencies in the pass band range are passed) and the stop band (in which signals of frequencies outside the pass band are attenuated) may be gradual or sharp, depending on the number of poles included in the filter's design. The poles are the roots of the denominator polynomial of the filter's transfer function and are known by those of ordinary skill in the art. Band pass filter 225 preferably includes eight poles, although more or fewer poles are permissible.

Threshold detector 227 of ventricular sense circuit 218 compares the signal provided to it by band pass filter 225 to a reference signal (not specifically shown) and provides an output signal to logic and control unit 230 on line 233. The output signal on line 233 generally indicates when the band pass filter's output signal exceeds the reference signal. The reference signal may be fixed or programmable by logic and control unit 230. The reference signal preferably is indicative of the minimum voltage level necessary to cause ventricular contraction. Thus, when the magnitude of the output signal of band pass filter 225 exceeds the magnitude of the reference signal, the ventricle likely is contracting. The output signal from threshold detector 227 may be encoded as a binary signal; that is, a logic high signal may indicate when the band pass filter's output exceeds the reference signal, and a logic low signal may indicate when the filter's output signal is below the reference signal.

Although the ventricular sense amplifier 220, band pass filter 225, and threshold detector 227 are shown as three separate components in the block diagram of FIG. 5, one of ordinary skill will recognize that these components may be combined into a single circuit or circuits, and this is typically the case for implantable pacemakers. For example, band pass filter 225 may be implemented using known switched capacitor technology that includes amplification for signals in the pass band of the filter. Also, ventricular sense amplifier 220, band pass filter 225, and threshold detector 227 may be provided in a different order than that shown. The arrangement of ventricular sense amplifier 220 and band pass filter 227, for example, may be reversed with band pass filter 225 coupled to the ventricular electrodes directly and then followed by ventricular sense amplifier 220.

Referring still to FIG. 5, atrial sense circuit 208 detects atrial electrical activity on line 161 and comprises atrial sense amplifier 210, band pass filter 215, comparators 240, 245, and threshold logic 250. Atrial sense amplifier 210 and band pass filter 215 preferably are of similar construction to the previously described ventricular sense amplifier 220 and band pass filter 225, respectively. As with the ventricular sense circuit 218, atrial sense amplifier 210 and band pass filter 215 may be combined into a single circuit or circuits, or may be provided in an order other than that shown in FIG. 5. It should be recognized, however, that the gain of atrial sense amplifier 210 and the frequency response of band pass filter 215 may be adjusted differently than for ventricular sense amplifier 220 and band pass filter 225. Different settings may be necessary to account for differences in the physiology of the atria as compared to the ventricles, as is understood by those skilled in the art.

Threshold detection in the atrial sense circuit is accomplished preferably by comparators 240, 245 and threshold logic 250. One of ordinary skill in the art will recognize that other circuit components, such as resistors, typically are included in comparator circuitry, and comparators 240, 245 would include such components but are not shown in the interest of clarity. Comparators 240, 245 thus represent exemplary schematics only and not complete circuitry.

Comparator 240 is configured as a positive threshold comparator and comparator 245 is configured as a negative threshold comparator. A positive reference voltage $+V_{TPOS}$ is provided to the inverting (−) terminal of comparator 240 and a negative reference voltage $-V_{TNEG}$ is provided to the non-inverting (+) terminal of comparator 245. The output signal on line 216 from band pass filter 215 is provided to both the non-inverting (+) terminal of comparator 240 and the inverting (−) terminal of comparator 245. When the atrial electrogram waveform is at a low positive or negative magnitude, the output signals from both comparators on lines 242 and 247 will be at a logic low level. However, when an event occurs, such as the P-wave as in FIG. 2, the magnitude of the electrogram may rise to a positive level greater than $+V_{TPOS}$. This condition forces the output signal on line 242 from comparator 240 to a logic high condition indicating the presence of an atrial event. Similarly, when the magnitude of the electrogram falls to a level more negative than $-V_{TNEG}$, the output signal on line 247 from comparator 245 also is forced to a logic high condition indicating the presence of an atrial event.

Figure 6:
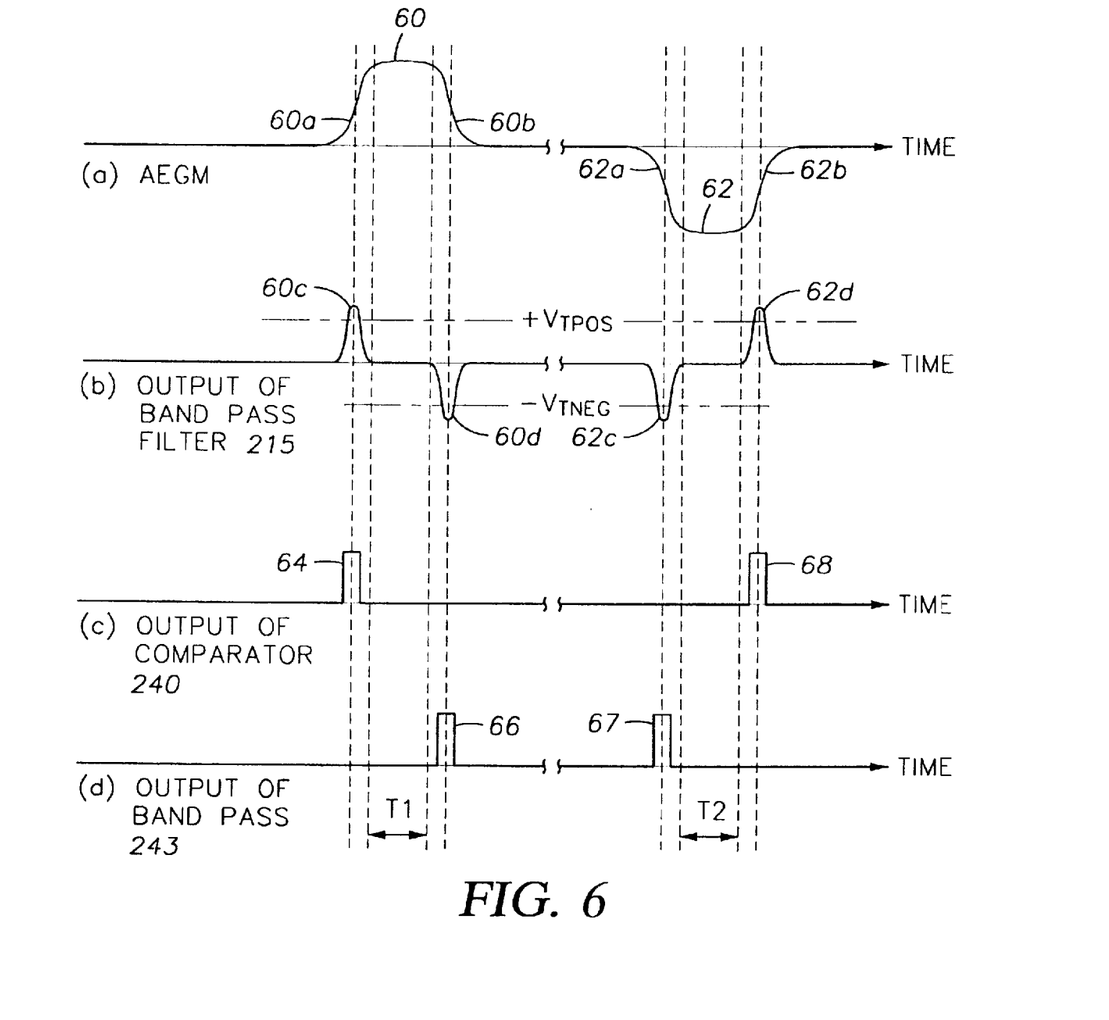

To fully appreciate the operation of threshold logic 250 to distinguish an atrial event representing a P-wave from atrial activity resulting from an ectopic beat, reference is made to FIGS. 5 and 6. The waveform in FIG. 6(a) represents an atrial electrogram including a positive pulse 60 and a negative pulse 62. The positive pulse 60 may be a P-wave such as shown in event 50 of FIG. 2 and the negative pulse 62 may include atrial detected activity from an ectopic beat as shown as activity 54a in FIG. 2. The trace in FIG. 6(b) represents the output signal from band pass filter 215 for which the trace in FIG. 6(a) is provided as an input signal.

As generally known by those skilled in the art, a band pass filter generally only passes signals with frequencies in the frequency range of the filter. Thus, if the filter includes a pass band of 20 to 60 Hz, signals in that frequency range are passed through the filter, while signals at all other frequencies (i.e., less than 20 Hz and greater than 60 Hz) are attenuated. The amplitude of positive pulse 60 and negative pulse 62 is substantially constant during times T1 and T2. A substantially constant signal has a low frequency approaching or equaling 0 Hz, outside the pass band of pass band filter 215. During times T1 and T2, the output signal from band pass filter 215 thus is 0 volts as shown in FIG. 6(b). The output signal from the filter 215, in fact, is non-zero only during the transitions in the AEGM waveform from low to high and high to low. Thus, during the low to high transition 60a in positive pulse 60, the output of the band pass filter is a spike 60c. The high to low transition 60b causes a negative voltage spike 60d to be produced by band pass filter 215 as those of ordinary skill would understand. Similarly, the high to low transition 62a of negative voltage pulse 62 causes a negative spike 62c to be produced by band pass filter 215, and the low to high transition 62b results in a positive filter output spike 62d.

FIGS. 6(c) and 6(d) show the resulting output pulses of comparators 240, 245, respectively. With the comparator threshold $+V_{TPOS}$ set at the level shown in FIG. 6(b), positive comparator 240 will be forced to a logic high state while the band pass filter's output voltage is greater than $+V_{TPOS}$, generally at positive filter spikes 60c and 62d. Thus, positive comparator 240 produces pulses 64, 68 shown in the trace of FIG. 6(c). Similarly, with $-V_{TNEG}$ set as shown in FIG. 6(b), negative comparator 245 produces pulses 66, 67 (FIG. 6(d)) when the output signal from band pass filter 215 becomes more negative than $-V_{TNEG}$, generally at negative spikes 60d and 62c.

Referring still to FIGS. 5 and 6, threshold logic 250 receives the output pulses from comparators 240, 245 on lines 242, 247, respectively. Threshold logic 250 examines the comparators' output signals and determines whether the associated atrial activity represents a normal P-wave or results from an ectopic beat detected remotely by the atrial electrodes. Threshold logic 250 preferably accomplishes this objective by determining which comparator produced the first pulse associated with the atrial event. With reference to FIGS. 6(c) and 6(d), if the first pulse from the comparators comes from positive comparator 240 (and is followed by a pulse from negative comparator 245), threshold logic 250 determines that the associated atrial event is a P-wave (event 60 in FIG. 6(a)). Conversely, if negative comparator 245 produces a pulse before comparator 240 produces its pulse, threshold logic 250 determines that the associated atrial event was merely the effects of an ectopic beat that was detected by the atrial electrodes.

Figure 7:
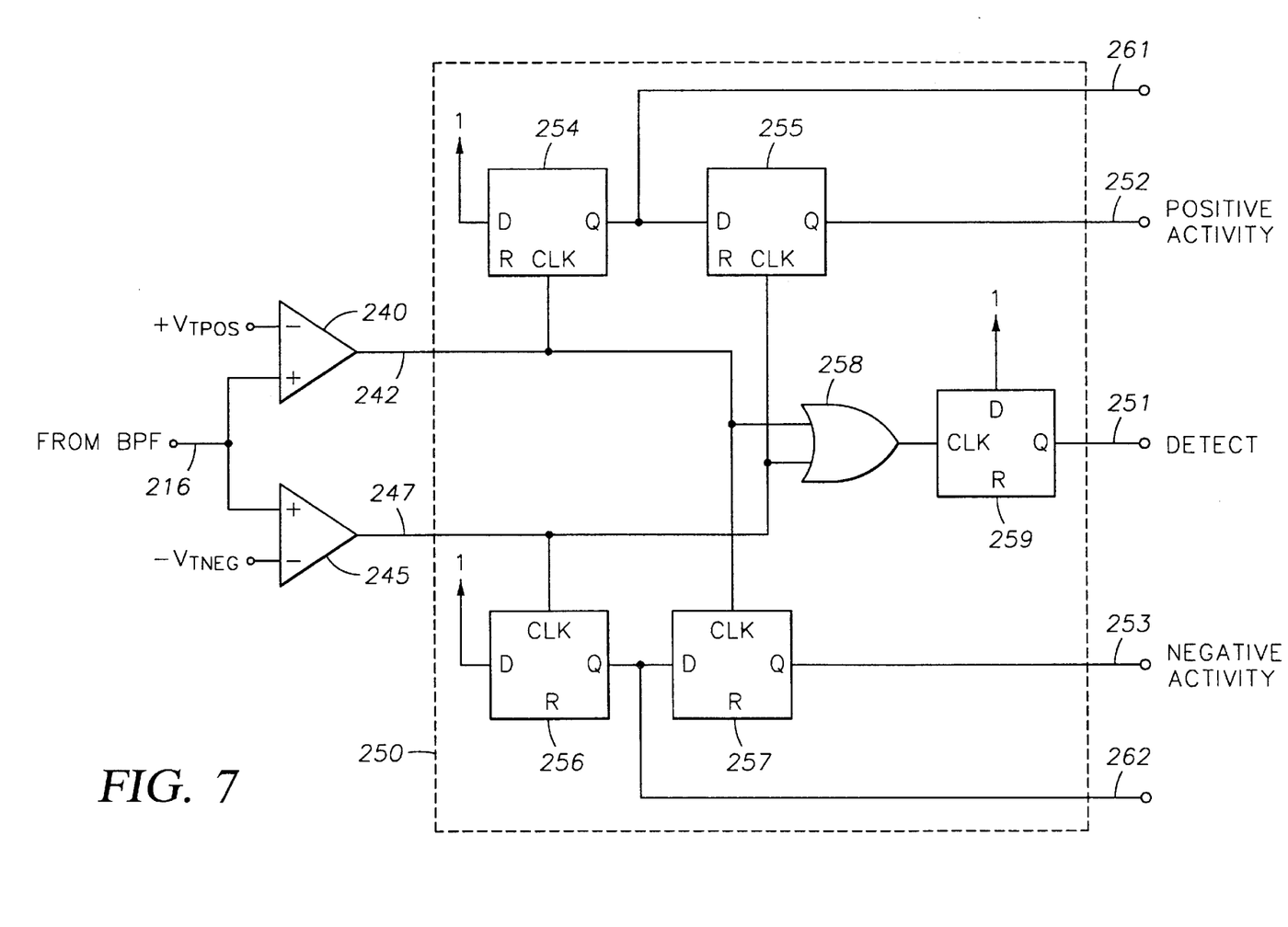
FIG. 7 is a schematic diagram of the threshold logic of the atrial sense circuit of FIG. 5 constructed in accordance with one embodiment of the present invention.

Although numerous embodiments of threshold logic 250 are possible and the present invention is intended to include all such embodiments, FIG. 7 includes a presently preferred circuit. It should also be recognized that the function performed by the threshold logic circuitry shown in FIG. 7 could be accomplished in software typically included in most pacers today. Comparators 240, 245 are shown at the left-hand side of FIG. 7 providing signals to the clock input pins (CLK) of latches 254, 255, 256, 257. Comparator 240 drives the CLK pin of latches 254 and 257, while comparator 245 drives the CLK pins of latches 256, 255. Latches 254, 255, 256, 257 may include D-flip flops as shown. A latch produces on its output pin Q a logic signal equivalent to the logic level present on its input D pin when a CLK signal is provided, for example, by a logic low to high transition. A latch thus "latches" on its output Q pin, the logic level present on its input D pin. Reset pins R are used to clear or reset the latches by reset circuitry not shown. Logic high signals are continuously provided to the input D terminals of latches 254, 256. When latches 254, 256 are clocked, the output Q terminals of the latches will become logic high states.

The output Q signals from latches 254, 256 are provided to the input D terminals of latches 255, 257. If latches 255, 257 are clocked subsequent to the activation of latches 54, 256, the output Q pin of latches 255, 257 will also become logic high values. The output signals from latches 255, 257 are provided as output signals on lines 252, 253 from threshold logic 250. The signal on line 252 is referred to as a positive activity signal and indicates the presence of positive polarity atrial activity (P-wave). The signal on line 252 is referred to as a negative activity signal and indicates the presence of negative polarity atrial activity resulting, for example, from a PVC.

An OR-gate 258 is also included to logically OR together the output signals from comparators 240, 245. The output signal from OR-gate 258 is also provided as an output signal from threshold logic 250 on line 251. OR-gate 258 provides a detect signal which merely indicates detected atrial activity (i.e., when either comparator registers activity).

The operation of threshold logic 250 shown in FIG. 7 will now be described to determine whether a positive polarity atrial voltage pulse (P-wave) is present in the atrial electrogram. It is assumed that all four latches initially are cleared and a logic low level is present on the output Q pins of each latch. The logic levels on output lines 252, 253, as well as the output of OR-gate 258 on line 251, are also low, indicating the absence of any atrial activity.

For a positive pulse, positive comparator 240 emits a voltage pulse 64 on the rising edge 60a of P-wave 60 followed by a pulse 66 from negative comparator 245 during the trailing edge 60b, as described above with reference to FIGS. 6 (a–d). Accordingly, the voltage pulse from comparator 240 clocks latches 254 and 257. With a logic high input on its D pin, the output of latch 254 goes high placing a logic high level on the D pin of latch 255. Because the input to latch 257 was a logic low level, the output of latch 257 remains at a logic low state.

When the subsequent voltage pulse is produced by comparator 245 on the trailing edge of P-wave 60, latches 256 and 255 are clocked. Because a logic high level is present on the D pin of latch 255, the output Q pin of latch 255 goes high producing a logic high state for the positive activity signal on line 252. Although the logic high signal on the D terminal of latch 256 is latched through to its Q pin, the logic level on the output Q pin of latch 257 remains unchanged and thus, the negative activity signal on line 253 remains at the logic low state.

At this point, the positive activity signal is high and the negative activity signal is low. By monitoring the state of these two signal, logic and control unit 230 can determine that the detected atrial event was a P-wave. Once the presence of a P-wave is detected, the latches are reset and positive activity and negative activity signals go to the logic low state.

The response of threshold logic 250 to an atrial event of negative polarity, such as negative pulse 62 in FIG. 6(a), is similar to that described above for positive P-wave pulses. In this situation, however, negative comparator 245 generates a voltage pulse 67 on the falling edge 62a of negative pulse 62 before positive comparator 240 generates a pulse 68 on the subsequent rising edge 62b. The voltage pulse 67 from comparator 245 clocks latches 256 and 255. With a logic high input on its D pin, the output of latch 256 goes high placing a logic high level on the D pin of latch 257. Because the input to latch 255 was a logic low level, the output signal from latch 255 remains at a logic low state.

When the subsequent voltage pulse 68 is produced by comparator 240 on the rising edge of P-wave 60, latches 254 and 257 are clocked. Because a logic high level is present on the D pin of latch 257, which was latched in during the preceding clocking of latch 256, the output Q pin of latch 257 goes high producing a logic high state for the negative activity signal on line 253. Although the logic high signal on the D terminal of latch 254 is latched through to its Q pin, the positive activity signal on line 252 remains at the logic low state.

At this point, the negative activity signal is high and the positive activity signal is low. Logic and control unit 230 thus determines that the atrial event was the result of an ectopic beat such as a PVC.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A medical device for electrically stimulating the heart, comprising:

a plurality of electrodes coupled to the heart;

a logic and control unit for initiating a pacing pulse to be delivered to the heart;

a pulse generator coupled to said logic and control unit, said pulse generator delivering a pacing pulse to the heart through said plurality of electrodes; and a sense circuit coupled to said logic and control for processing electrical activity detected in a chamber of the heart, said electrical activity including transitions between signal levels, said sense circuit including:

a band pass filter producing an output signal corresponding to transitions in said electrical activity;

a threshold detector capable of determining whether an electrical event detected in a chamber of the heart resulted from an ectopic beat and including a positive comparator and a negative comparator, wherein said positive comparator produces a pulse when said output signal from said band pass filter becomes more positive than a positive threshold level and said negative comparator produces a pulse when said output signal becomes more negative than a negative threshold level; and threshold logic that includes input signals received from said positive and negative comparators and that provides output signals to said logic and control unit indicative of which comparator produced a pulse first.

2. The medical device of claim 1 wherein said output signals from said threshold logic include a positive activity signal and a negative activity signal, wherein said positive activity signal becomes active when said positive comparator produces an output pulse before an output pulse is produced by said negative comparator.

3. The medical device of claim 2 wherein said negative activity signal becomes active when said negative comparator produces an output pulse before an output pulse is produced by said positive comparator.

4. The medical device of claim 3 wherein said threshold logic includes a plurality of latches.

5. The medical device of claim 4 wherein said plurality of latches include clock terminals and said positive and negative comparators couple to said clock terminals of said latches.

6. The medical device of claim 5 wherein a positive activity signal is produced on an output terminal of one of said plurality of latches, and a negative activity signal is produced on an output terminal of another of said plurality of latches.

7. A method for distinguishing a P-wave from an ectopic beat using an implantable medical device and an electrode implanted in the atrium of the heart for sensing electrical activity in the atrium and providing a representative signal to the implantable medical device, said method comprising:

(a) filtering the signal representation of electrical activity in the atrium through a band pass filter to produce an output signal;

(b) comparing said output signal from said band pass filter to predetermined positive and negative threshold levels using a first threshold comparator and a second threshold comparator;

(c) producing an output pulse from a given one of said threshold comparators when said output signal from said band pass filter exceeds the threshold level of said given threshold comparator; and (d) determining which of said comparators first produced an output pulse.

8. The method of claim 7 further including the step of:

(e) determining that said electrical activity includes a P-wave when said first threshold comparator produces a pulse before said second threshold comparator.

9. The method of claim 8 further including the step of:

(e) determining that said electrical activity resulted from an ectopic beat when said second threshold comparator produces a pulse before said first threshold comparator.

* * * * *